United States Patent
Nishibayashi et al.

(10) Patent No.: US 6,913,575 B2
(45) Date of Patent: Jul. 5, 2005

(54) BLOOD PRESSURE MEASURING APPARATUS

(75) Inventors: Hideo Nishibayashi, Komaki (JP); Toshihiko Ogura, Komaki (JP)

(73) Assignee: Colin Medical Technology Corporation, Komaki (JP)

(*) Notice: Subject to any disclaimer, the term of this patent is extended or adjusted under 35 U.S.C. 154(b) by 0 days.

(21) Appl. No.: 10/397,424

(22) Filed: Mar. 27, 2003

(65) Prior Publication Data

US 2004/0024325 A1 Feb. 5, 2004

(30) Foreign Application Priority Data

Aug. 5, 2002 (JP) .................................. 2002-228007
Dec. 20, 2002 (JP) .................................. 2002-370022

(51) Int. Cl.[7] .............................................. A61B 5/02
(52) U.S. Cl. ........................ 600/490; 600/485; 600/499
(58) Field of Search ........................ 600/485, 490–504, 600/507

(56) References Cited

U.S. PATENT DOCUMENTS

| | | | | |
|---|---|---|---|---|
| 3,157,177 A | * | 11/1964 | Smith ........................ 600/492 |
| 3,348,534 A | * | 10/1967 | Marx et al. ................ 600/492 |
| 3,581,734 A | * | 6/1971 | Croslin et al. ............. 600/492 |
| 4,649,928 A | * | 3/1987 | Samaras et al. ........... 600/492 |
| 4,729,382 A | * | 3/1988 | Schaffer et al. ........... 600/492 |
| 4,858,616 A | * | 8/1989 | Samaras et al. ........... 600/493 |
| 4,920,971 A | * | 5/1990 | Blessinger ................ 600/492 |
| 4,928,674 A | * | 5/1990 | Halperin et al. ........... 601/44 |
| 5,842,996 A | * | 12/1998 | Gruenfeld et al. ......... 600/490 |
| 6,346,083 B1 | | 2/2002 | Nishibayashi et al. ..... 600/490 |
| 6,497,668 B2 | | 12/2002 | Nishibayashi ............. 600/494 |

FOREIGN PATENT DOCUMENTS

| | | | |
|---|---|---|---|
| EP | 1 080 685 A1 | 3/2001 | |
| EP | 1 159 914 A2 | * 5/2001 | ........... A61B/5/022 |
| EP | 1 159 914 A2 | 12/2001 | |
| JP | A 05-269089 | 10/1993 | |
| JP | A 5-269089 | 10/1993 | |
| JP | A 2001-70262 | 3/2001 | |
| JP | A 2001-333888 | 12/2001 | |

* cited by examiner

*Primary Examiner*—Max F. Hindenburg
*Assistant Examiner*—Patricia C. Mallari
(74) *Attorney, Agent, or Firm*—Oliff & Berridge, PLC

(57) ABSTRACT

A blood pressure measuring apparatus having an inflatable cuff including a first inflatable bag adapted to be worn on a body portion of a living subject so as to exclude blood from an artery located in the body portion, and a second inflatable bag adapted to be worn on the body portion, on a distal side of a middle portion of the first inflatable bag, so as to detect a pulse wave produced from the artery, a first piping which is connected to the first inflatable bag, a second piping which is branched from the first piping and is connected to the second inflatable bag, a pump which supplies an inflating fluid to the first and second inflatable bags via the first and second pipings, respectively, a blood pressure determining device which determines a blood pressure of the subject based on the pulse wave detected through the second inflatable bag when a pressing pressure of the first inflatable bag is changed, and a switching device which is provided in the second piping and which selectively switches the second piping to a connected state in which the second piping is connected to the first piping and to a disconnected state in which the second piping is disconnected from the first piping.

5 Claims, 8 Drawing Sheets

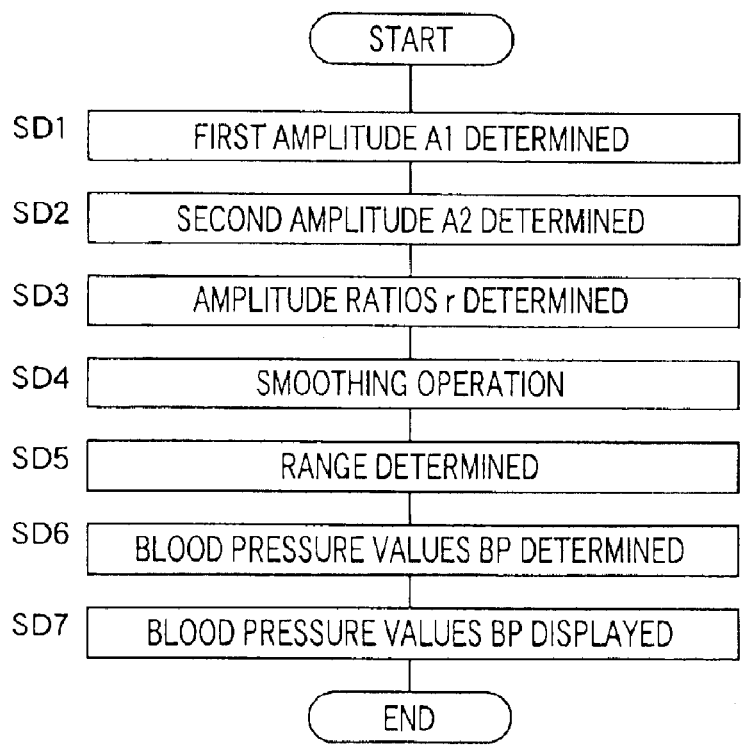

BLOOD PRESSURE MEASURING APPARATUS

BACKGROUND OF THE INVENTION

1. Field of the Invention

The present invention relates to an oscillometric-type blood pressure measuring apparatus and particularly to such a blood pressure measuring apparatus comprising a cuff including two inflatable bags.

2. Related Art Statement

Generally, an oscillometric-type blood pressure measuring apparatus includes a cuff which is adapted to be wound around a body portion of a living subject and includes an inflatable bag; a pressure changing device which increases a pressing pressure of the inflatable bag up to a prescribed pressure value which could completely exclude blood from an artery present under the cuff, and subsequently slowly decreases the pressure in the bag at a prescribed rate; a pressure sensor which continuously detects the pressure in the bag during the slow deflation of the bag; a pulse-wave filter which extracts a pulse wave from the pressure in the bag, continuously detected by the pressure sensor; and a means for determining, as a blood pressure of the subject, a pressure in the bag at a time of occurrence of a prescribed change of respective amplitudes of successive heartbeat-synchronous pulses of the extracted pulse wave.

More specifically described, the above-indicated blood pressure measuring apparatus determines, as a systolic blood pressure of the subject, a static pressure of the inflatable bag at a time of detection of a rising point where the respective amplitudes of successive heartbeat-synchronous pulses of the pulse wave continuously detected during the slow decreasing of the pressure of the bag, significantly largely increase.

However, the blood pressure measuring apparatus has the problem that since only the single inflatable bag is provided in the cuff and accordingly the rising point of the amplitudes of the pulse wave, successively determined from the change of pressure in the bag, is not clear, the determined systolic blood pressure of the subject may not be accurate. The reason is that even if the pressing pressure of the cuff may be higher than the systolic blood pressure of the subject, as the pressure of the cuff approaches the systolic blood pressure, the pulsation of the artery under the cuff starts under a proximal or upstream end portion of the cuff and propagates to the cuff. In particular, in the case where the body portion, such as ankle, around which the cuff is wound is difficult to completely exclude the blood from the artery thereof, the pulsation of the artery is likely to be large even if the pressure of the cuff may be higher than the systolic blood pressure of the subject. Therefore, the rising point of the amplitudes of the pulse wave is likely to be unclear.

To solve the above-indicated problem, it has been proposed to provide a blood pressure measuring apparatus that measures a blood pressure using a cuff including two inflatable bags one of which is used for excluding blood from an artery and the other of which is used for detecting a pulse wave from the artery. Japanese patent document No. 5-269089 discloses an example of the blood pressure measuring apparatus. The apparatus disclosed by the Japanese patent document employs an inner cuff as an inflatable bag for detecting a pulse wave, the inner cuff being provided on substantially the middle portion of the inner surface (i.e., body-side surface) of an outer cuff as an inflatable bag for excluding blood. Therefore, even if the arterial pulsation may resume around the upstream end portion of the outer cuff, the pulsation does not directly propagate to the inner cuff, so that the amplitudes of the pulse wave detected from the inner cuff show a clear rising point, which contributes to improving the accuracy of measurement of systolic blood pressure of the subject.

However, even in the case where a pulse wave is detected by a pulse-wave detecting inflatable bag that is provided independent of a blood excluding inflatable bag, respective amplitudes of heartbeat-synchronous pulses of the pulse wave may not show a clear rising point, because the pulsation of an artery that propagates to the blood excluding bag in the state in which the pressing pressure of the blood excluding bag is higher than a systolic blood pressure of a living subject, further propagates from the blood excluding bag to the pulse-wave detecting bag. Therefore, even if a systolic blood pressure may be determined based on the change of respective amplitudes of heartbeat-synchronous pulses of the pulse wave detected by the pulse-wave detecting bag, the determined systolic blood pressure may not be accurate.

The apparatus disclosed by the above-indicated Japanese patent document employs an oscillation shielding plate between the blood excluding bag and the pulse-wave detecting bag, for preventing the pulsation of artery from propagating from the blood excluding bag to the pulse-wave detecting bag. In addition, since a tube (or a pipe) employed for supplying a liquid (i.e., an inflating fluid) to the pulse-wave detecting bag is branched from a tube (or a pipe) employed for supplying the liquid to the blood excluding bag, the pulsation of artery that propagates to the blood excluding bag may further propagate via the two tubes to the pulse-wave detecting bag. To solve this problem, the tube for supplying the liquid to the pulse-wave detecting bag is thinner than the tube for supplying the liquid to the blood excluding bag. Since, however, the arterial pulsation that propagates to the blood excluding bag partly propagates via the two tubes to the pulse-wave detecting bag, the amplitudes of pulses of the pulse wave detected through the pulse-wave detecting bag may not show a sufficiently clear rising point.

SUMMARY OF THE INVENTION

It is therefore an object of the present invention to provide a blood pressure measuring apparatus which can measure an accurate systolic blood pressure of a living subject.

The above object has been achieved by the present invention. According to the present invention, there is provided a blood pressure measuring apparatus comprising an inflatable cuff including a first inflatable bag adapted to be worn on a body portion of a living subject so as to exclude blood from an artery located in the body portion, and a second inflatable bag adapted to be worn on the body portion, on a distal side of a middle portion of the first inflatable bag, so as to detect a pulse wave produced from the artery; a first piping which is connected to the first inflatable bag; a second piping which is branched from the first piping and is connected to the second inflatable bag; a pump which supplies an inflating fluid to the first and second inflatable bags via the first and second pipings, respectively; a blood pressure determining device which determines a blood pressure of the subject based on the pulse wave detected through the second inflatable bag when a pressing pressure of the first inflatable bag is changed; and a switching device which is provided in the second piping and which selectively switches the second piping to a connected state in which the second piping is connected to the first piping and to a disconnected state in which the second piping is disconnected from the first piping.

According to the present invention, if the switching device switches the second piping to the connected state, the inflating fluid supplied from the pump is supplied to the second inflatable bag and then, if the switching device switches the second piping to the disconnected state, the arterial pulsation that propagates from the artery located in the body portion where the cuff is worn, to the first inflatable bag, does not propagate to the second inflatable bag via the first piping and the second piping. Therefore, the respective amplitudes of heartbeat-synchronous pulses of the pulse wave detected through the second inflatable bag show a clear change, which contributes to improving the accuracy of measurement of systolic blood pressure of the subject.

The time when the pressing pressure of the first inflatable bag becomes equal to the systolic blood pressure of the subject during the changing of the pressure of the first bag, may be determined based on respective amplitude differences, or respective amplitude ratios, between respective amplitudes of respective heartbeat-synchronous pulses of a first pulse wave detected through the first inflatable bag, and respective amplitudes of respective heartbeat-synchronous pulses of a second pulse wave detected through the second inflatable bag. Since an oscillatory component representing an arterial pulsation that propagates from the first bag to the second bag can be removed from the second pulse wave detected through the second bag, by using the above-indicated amplitude differences or amplitude ratios, the second pulse wave can show a clear rising point.

The manner in which the time when the pressing pressure of the first inflatable bag becomes equal to the systolic blood pressure of the subject is determined based on the amplitude differences, is as follows: First, either respective second amplitudes of respective pulses of the second pulse wave detected through the second inflatable bag, or respective first amplitudes of respective pulses of the first pulse wave detected through the first inflatable bag are corrected using an appropriate correction factor. Then, respective differences between the thus corrected amplitudes and the non-corrected amplitudes are calculated. Finally, the above-indicated time is determined based on the change of the thus calculated amplitude differences. This manner is disclosed by Japanese patent document No. 2001-070262.

According to a preferred feature of the present invention in which the above manner is employed, the blood pressure determining device comprises an amplitude correcting means for correcting at least one of respective first amplitudes of respective heartbeat-synchronous pulses of a first pulse wave detected through the first inflatable bag when the pressing pressure of the first inflatable bag is decreased in a blood-flow stopping pressure range in which a flow of blood in the artery is stopped, and respective second amplitudes of respective heartbeat-synchronous pulses of a second pulse wave detected through the second inflatable bag when the pressing pressure of the first inflatable bag is decreased in the blood-flow stopping pressure range, so that each of the corrected amplitudes is substantially equal to a corresponding amplitude of the other of the first amplitudes and the second amplitudes; an amplitude-difference determining means for determining an amplitude difference between the each of the corrected amplitudes and the corresponding amplitude of the other of the first amplitudes and the second amplitudes, so that the determined amplitude differences show a rising point; and a blood pressure determining means for determining a systolic blood pressure of the subject based on the rising point of the amplitude differences determined by the amplitude-difference determining means.

In the blood pressure measuring apparatus constructed as described above, the amplitude correcting means corrects at least one of the amplitudes of pulses of the first pulse wave detected through the first inflatable bag when the pressure of the first bag is changed in the blood-flow stopping pressure range in which the flow of blood in the artery of the body portion where the cuff is wound is stopped, and the amplitudes of pulses of the second pulse wave detected through the second inflatable bag when the pressure of the first bag is changed in the blood-flow stopping pressure range, so that each of the corrected amplitudes is substantially equal to a corresponding amplitude of the other of the first amplitudes and the second amplitudes, and the amplitude-difference determining means determines an amplitude difference between the each of the corrected amplitudes and the corresponding amplitude of the other of the first amplitudes and the second amplitudes, so that the determined amplitude differences show a clear rising point. Finally, the blood pressure determining means determines a systolic blood pressure of the subject based on the rising point of the amplitude differences determined by the amplitude-difference determining means. Therefore, the thus determined systolic blood pressure enjoys a high accuracy.

Also, the manner in which the time when the pressing pressure of the first inflatable bag becomes equal to the systolic blood pressure of the subject is determined based on the change of the amplitude ratios, is disclosed by Japanese patent document No. 2001-333888.

According to another feature of the present invention in which the above manner is employed, the blood pressure determining device comprises a first amplitude determining means for determining respective first amplitudes of respective heartbeat-synchronous pulses of a first pulse wave detected through the first inflatable bag when the pressure of the first inflatable bag is changed; a second amplitude determining means for determining respective second amplitudes of respective heartbeat-synchronous pulses of a second pulse wave detected through the second inflatable bag when the pressure of the first inflatable bag is changed; an amplitude-ratio determining means for determining an amplitude ratio between each of the first amplitudes determined by the first amplitude determining means and a corresponding one of the second amplitudes determined by the second amplitude determining means; and a blood pressure determining means for determining a systolic blood pressure of the subject based on the amplitude ratios determined by the amplitude-ratio determining means.

According to this feature, the first amplitude determining means determines the first amplitudes of the pulses of the first pulse wave detected through the first inflatable bag when the pressure of the first bag is changed; the second amplitude determining means determines the second amplitudes of the pulses of the second pulse wave detected through the second inflatable bag when the pressure of the first bag is changed; the amplitude-ratio determining means determines the amplitude ratio between the each of the first amplitudes and the corresponding one of the second amplitudes; and the blood pressure determining means determines the systolic blood pressure of the subject based on the amplitude ratios. When the pressing pressure of the first inflatable bag is higher than the systolic blood pressure of the subject, the second inflatable bag worn on the body portion on the downstream side of the middle portion of the first bag, only receives the pulse wave that propagates thereto indirectly, i.e., via the first bag. Therefore, the second amplitudes are small. Meanwhile, when the pressure of the first bag is not higher than the systolic blood pressure, the second bag receives not just the pulse wave that propagates thereto indirectly, but also a pulse wave that directly propagates thereto from the artery. Therefore, the second amplitudes are large. On the other hand, when the pressing pressure of the first inflatable bag is higher than the systolic blood pressure, an upstream-side portion of the first bag receives a pressure pulse wave that propagates thereto from the artery. Therefore, the first amplitudes do not change so largely at the systolic blood pressure as the second amplitudes. Thus, the above-indicated amplitude ratios change largely at the systolic blood pressure. Since the blood pressure determining means determines the systolic blood pressure of the subject based on the amplitude ratios, the thus determined systolic blood pressure can enjoy a high accuracy.

As described above, based on the amplitude differences, or the amplitude ratios, between the amplitudes of the pulses of the first pulse wave detected through the first inflatable bag, and the amplitudes of the pulses of the second pulse wave detected through the second inflatable bag, the oscillatory component representing the arterial pulsation that propagates from the first bag to the second bag, can be removed from the second pulse wave detected through the second bag, and accordingly the amplitudes of the pulses of the second pulse wave show a clear rising point. However, in the blood pressure measuring apparatus according to the present invention, the second piping can be disconnected, by the switching device, from the first piping, so as to minimize the influences from the first inflatable bag and the first piping. Therefore, it is not essentially needed to calculate the amplitude differences, or the amplitude ratios, between the amplitudes of the pulses of the first pulse wave detected through the first inflatable bag, and the amplitudes of the pulses of the second pulse wave detected through the second inflatable bag. Without the amplitude differences or the amplitude ratios, it is possible to determine the time when the pressing pressure of the first inflatable bag becomes equal to the systolic blood pressure of the subject, based on the change of the amplitudes of the pulses of the second pulse wave detected through the second inflatable bag. Even in this manner, the blood pressure measuring apparatus according to the present invention can assure that the amplitudes of the pulses of the second pulse wave detected through the second inflatable bag show a clear change, and accordingly it can measure a highly accurate systolic blood pressure of the subject.

BRIEF DESCRIPTION OF THE DRAWINGS

The above and optional objects, features, and advantages of the present invention will be better understood by reading the following detailed description of preferred embodiments of the invention when considered in conjunction with the accompanying drawings, in which:

FIG. 8 is a flow chart representing a portion of the essential control functions of the CPU, shown in FIG. 7, that is, a signal processing routine.

DETAILED DESCRIPTION OF PREFERRED EMBODIMENTS

Figure 1:
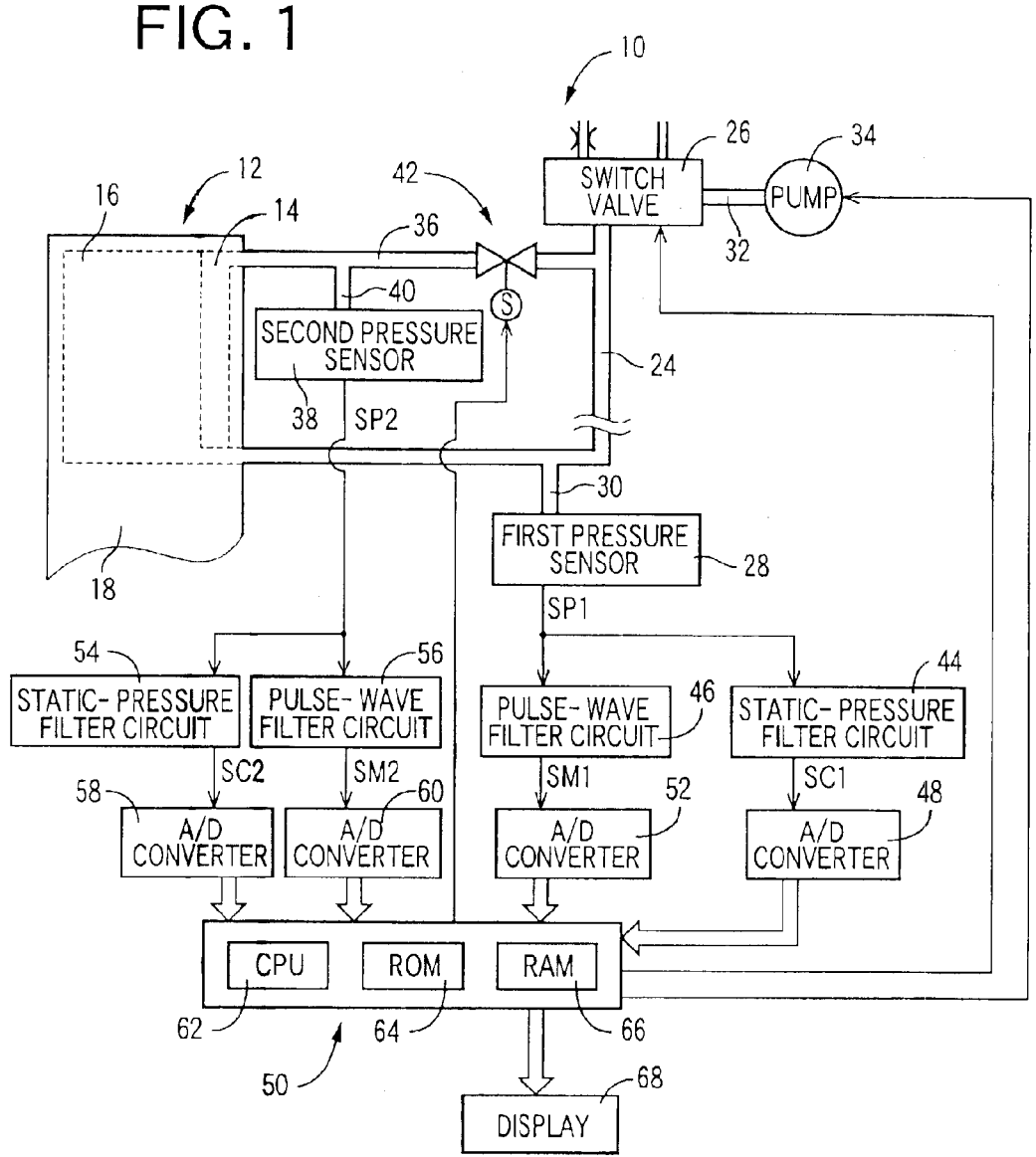
FIG. 1 is a diagrammatic view for explaining a circuitry of a blood pressure measuring apparatus embodying the present invention.

Hereinafter, there will be described an embodiment of the present invention, by reference to the drawings. FIG. 1 is a diagrammatic view for explaining the construction of a blood pressure measuring apparatus 10 to which the present invention is applied.

Figure 2:
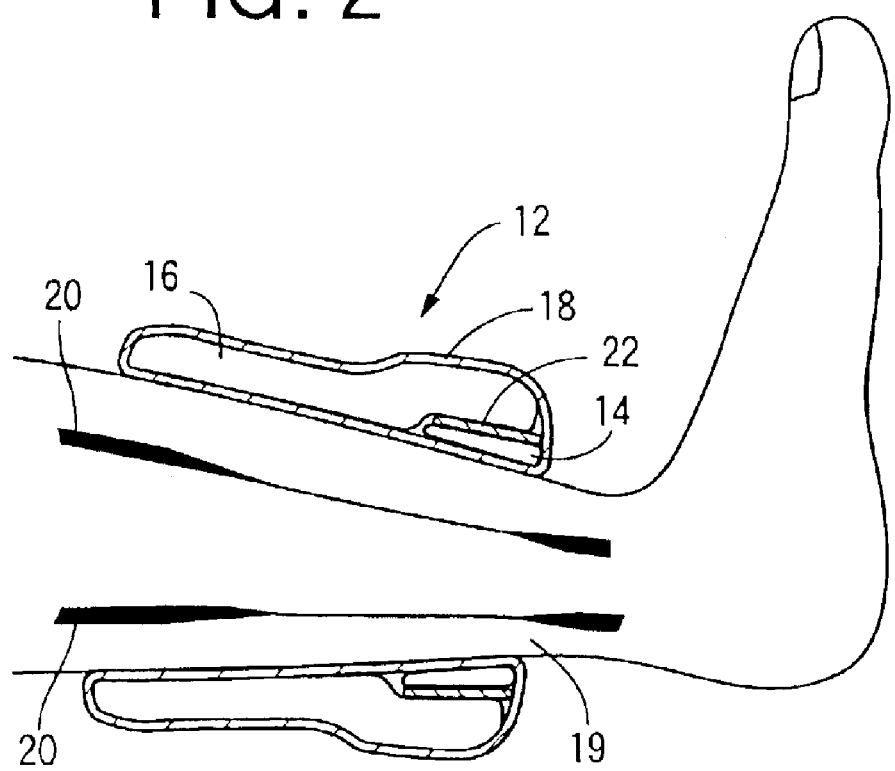
FIG. 2 is a view showing a state in which a cuff shown in FIG. 1 is wound around an ankle of a living subject and an artery of the ankle is occluded by the cuff.

In FIG. 1, the blood pressure measuring apparatus 10 includes an inflatable cuff 12 which is adapted to be wound around an ankle 19 of a living subject, as shown in FIG. 2. The present cuff 12 differs from a cuff which is commonly used to measure a blood pressure value of an ankle of a living subject, in that the cuff 12 has a second rubber bag 14 that functions as a second inflatable bag.

More specifically described, the cuff 12 includes a first rubber bag 16 that functions as a first inflatable bag and is used for pressing an artery of the ankle where the cuff 12 is worn and thereby excluding blood from the artery; the second rubber bag 14 that functions as a second inflatable bag and is used for detecting a pulse wave from the artery where the cuff 12 is worn; and a belt-like bag 18 that accommodates both the first and second rubber bags 16, 14.

The belt-like bag 18 has a shape that is advantageously wound around an ankle of a living subject, and is formed of a cloth that is non-stretchable and has a considerably high rigidity. The first rubber bag 16 has a prescribed width somewhat shorter than that of the belt-like bag 18, and a prescribed length shorter than a circumferential length of the ankle (e.g., the length of the first rubber bag 16 is equal to about two thirds of an average circumferential length of ankle).

The second rubber bag 14 is provided in a distal-side or downstream-side end portion of the belt-like bag 18, and on an inner side of the first rubber bag 16 (i.e., on the side of the ankle 19), in a state in which the cuff 12 is wound around the ankle 19. The second rubber bag 14 has a prescribed length substantially equal to that of the first rubber bag 16, and has a prescribed width not greater than one second of that of the same 16 (the width of the second bag 14 is equal to, e.g., one fourth to one sixth of the width of the first bag 16).

FIG. 2 shows a state in which the cuff 12 constructed as described above is wound around the ankle 19 of the living subject and is inflated to exclude blood from an artery 20 of the ankle 19. As shown in FIG. 2, a shield plate 22 is provided between the first rubber bag 16 and the second rubber bag 14, for preventing oscillation produced in the first bag 16, from being transmitted to the second bag 14. The shield plate 22 has prescribed width and length substantially equal to those of the second rubber bag 14, and is formed of a considerably hard, flexible material having a thickness of about 0.3 mm. In FIG. 1, the shield plate 22 of the cuff 12 is not shown.

The first rubber bag 16 is connected via a first piping 24 to a switch valve 26. A first pressure sensor 28 is connected via a branch piping 30 of the first piping 24 to the first rubber bag 16 and the switch valve 26. The switch valve 26 is connected via a piping 32 to an air pump 34.

The second rubber bag 14 is connected to a second piping 36 as another branch piping of the first piping 24 that braches from the first piping 24, at a position nearer to the switch valve 26 than a position where the branch piping 30 branches from the first piping 24. A second pressure sensor 38 is connected via a branch piping 40 of the second piping 36 to the second rubber bag 14 and the switch valve 26. In addition, a solenoid valve 42 functioning as a switching device is provided in the second piping 36, at a position nearer to the switch valve 26 than a position where the branch piping 40 branches from the second piping 36. The first piping 24, the second piping 36, and the branch pipings 30, 40 have the same diameter.

The switch valve 26 is selectively placed in one of the following three positions: the first position is a pressure-supply position in which the valve 26 permits pressurized air to be supplied from the air pump 34 to the cuff 12 (i.e., the first and second rubber bags 16, 14); the second position is a slow-deflation position in which the valve 26 permits the pressurized air to be slowly deflated from the cuff 12; and the third position is a quick-deflation position in which the valve 26 permits the pressurized air to be quickly deflated from the cuff 12.

The first pressure sensor 28 detects a first pressure P1 in the first rubber bag 16, and supplies a first pressure signal SP1 representing the detected first pressure P1, to each of a static-pressure filter circuit 44 and a pulse-wave filter circuit 46. The static-pressure filter circuit 44 includes a low-pass filter which extracts, from the first pressure signal SP1, a first cuff pressure signal SC1 representing a static component of the signal SP1, i.e., a pressing pressure of the first rubber bag 16 (hereinafter, referred to as the first cuff pressure PC1), and supplies the first cuff pressure signal SC1 to an electronic control device 50 via an A/D (analog-to-digital) converter 48. The pulse-wave filter circuit 46 includes a band-pass filter which extracts, from the first pressure signal SP1, a first pulse wave signal SM1 representing a first cuff pulse wave as a frequency component of the signal SP1, and supplies the first pulse wave signal SM1 to the control device 50 via an A/D converter 52.

The solenoid valve 42 is selectively switched, according to a control signal supplied from the control device 50, to an opening position (i.e., a connecting position) and a closing position (i.e., a disconnecting position).

The second pressure sensor 38 detects a second pressure P2 in the second rubber bag 14, and supplies a second pressure signal SP2 representing the detected second pressure P2, to a second static-pressure filter circuit 54 and a second pulse-wave filter circuit 56. The second static-pressure filter circuit 54 and the second pulse-wave filter circuit 56 have the same constructions as those of the first static-pressure filter circuit 44 and the first pulse-wave filter circuit 46, respectively. The second static-pressure filter circuit 54 extracts, from the second pressure signal SP2, a second cuff pressure signal SC2 representing a static component of the signal SP2, i.e., a pressing pressure of the second rubber bag 14 (hereinafter, referred to as the second cuff pressure PC2), and supplies the second cuff pressure signal SC2 to the control device 50 via an A/D converter 58; and the second pulse-wave filter circuit 56 extracts, from the second pressure signal SP2, a second pulse wave signal SM2 representing a second pulse wave as a frequency component of the signal SP2, and supplies the second pulse wave signal SM2 to the control device 50 via an A/D converter 60.

The control device 50 is essentially provided by a so-called microcomputer including a CPU (central processing unit) 62, a ROM (read only memory) 64, a RAM (random access memory) 66, an I/O (input-and-output) port, not shown, etc. The CPU 62 processes signals according to control programs pre-stored in the ROM 64, while utilizing a temporary-storage function of the RAM 66, and outputs, via the I/O port, drive signals to the switch valve 26, the air pump 34, and the solenoid valve 42, and thereby controls those elements 26, 34, 42. In addition, the CPU 62 determines a blood pressure value or values BP of the living subject based on the first cuff pressure signal SC1 supplied from the first static-pressure filter circuit 44 and the second pulse wave signal SM2 supplied from the second pulse-wave filter circuit 56. Moreover, the control device 50 controls a display device 68 to display the thus determined blood pressure values of the living subject.

Figure 3:
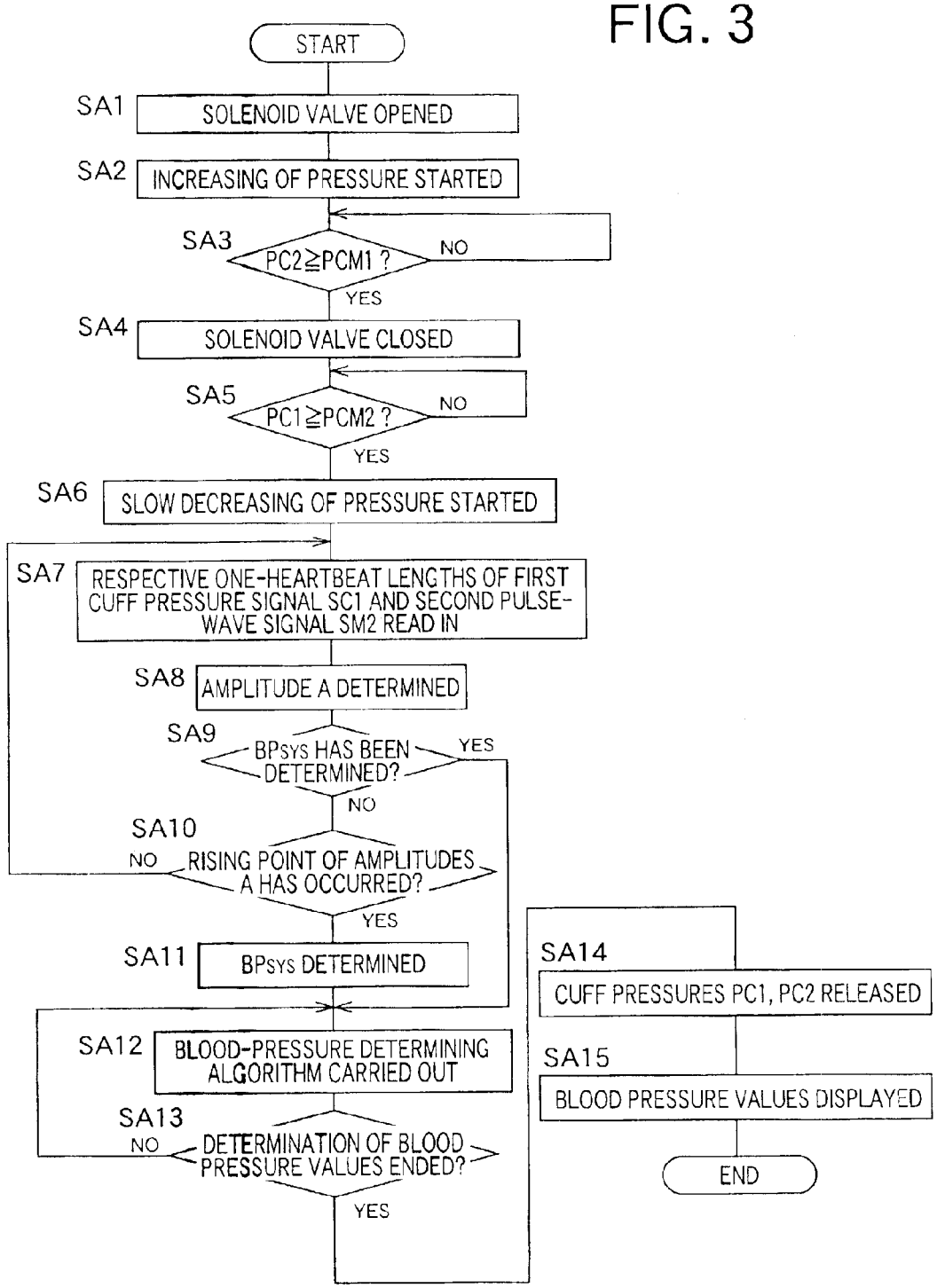
FIG. 3 is a flow chart representing essential control functions of a CPU (central processing unit) of the blood pressure measuring apparatus of FIG. 1.

FIG. 3 is a flow chart representing the essential control functions of the CPU 62. First, the CPU carries out Step SA1 (hereinafter, "Step" is omitted) to place the solenoid valve 42 to its opening position.

Subsequently, at SA2, the CPU operates the air pump 34 and places the switch valve 26 to its pressure-supply position, so as to start supplying the pressurized air as an inflating fluid to the first and second rubber bags 16, 14 and thereby start increasing the respective inner pressures of the two rubber bags 16, 14.

At SA3, the CPU judges whether the second cuff pressure PC2 represented by the second cuff pressure signal SC2 supplied from the second static-pressure filter circuit 54 has reached a prescribed first target pressure PCM1. The first target pressure PCM1 is prescribed at a pressure that assures that the second rubber bag 14 is so largely inflated as to be able to detect the pulse wave transmitted thereto from the artery 20 (i.e., the second cuff pulse wave represented by the second pulse-wave signal SM2 supplied from the second pulse-wave filter circuit 56). For example, the first target pressure PCM1 is prescribed at a pressure of 50 mmHg that would be somewhat lower than a diastolic blood pressure $BP_{DIA}$ of the subject.

If a negative judgment is made at SA3, SA3 is repeated, while the first and second cuff pressures PC1, PC2 are continuously increased. On the other hand, if a positive judgment is made at SA3, the control of the CPU proceeds with SA4 to place the solenoid valve 42 in its closing position. Thus, the second cuff pressure, PC2 is maintained at the first target cuff pressure PCM1, but the first cuff pressure PC1 is further increased.

At SA5, the CPU judges whether the first cuff pressure PC1 has reached a prescribed second target pressure PCM2 (e.g., 240 mmHg) as a pressing pressure which can stop the flow of blood in the artery 20 under the cuff 12. If a negative judgment is made at SA5, SA5 is repeated, while the first cuff pressure PC1 is further increased.

On the other hand, if a positive judgment is made at SA5, the control of the CPU proceeds with SA6 to stop the operation of the air pump 34 and switch the switch valve 26 to its slow-deflation position, so as to slowly decrease the pressing pressure of the first rubber bag 16, i.e., the first cuff pressure PC1 at a prescribed rate of 3 mmHg/sec.

SA6 is followed by SA7 where the CPU reads in respective one-heartbeat lengths of the first cuff-pressure signal SC1 supplied from the first static-pressure filter circuit 44 and the second pulse-wave signal SM2 supplied from the second pulse-wave filter circuit 56. Subsequently, at SA8, the CPU determines an amplitude A of a heartbeat-synchronous pulse of the second cuff pulse wave represented by the second pulse-wave signal SM2 read in at SA7. An amplitude of each heartbeat-synchronous pulse is defined as the difference between a maximum magnitude and a minimum magnitude of the each pulse.

Then, at SA9, the CPU judges whether a systolic blood pressure $BP_{SYS}$ of the subject has been determined already. If a positive judgment is made at SA9, the control of the CPU proceeds with SA12 and the following steps, described later. On the other hand, if a negative judgment is made at SA9, the control proceeds with SA10 to judge whether a rising point of the respective amplitudes A of the respective heartbeat-synchronous pulses of the second cuff pulse wave has occurred. More specifically described, the CPU calculates a rate of change d, or an amount of change $\Delta A$, of the current amplitude A determined at SA8 in the current cycle, from the preceding amplitude A determined at SA8 in the preceding cycle, and judges that the rising point has occurred if the rate of change d or the amount of change $\Delta A$ is greater than a prescribed threshold value.

A positive judgment made at SA10 indicates that the first cuff pressure PC1 has decreased down to a systolic blood pressure $BP_{SYS}$ of the artery 20 and the flow of blood through the artery 20 has resumed. Hence, the control of the CPU goes to SA11 to determine, as the systolic blood pressure $BP_{SYS}$ of the subject, a value of the first cuff pressure PC1 at the time when the positive judgment is made at SA10. On the other hand, if a negative judgment is made at SA10, the control goes back to SA7 and the following steps.

If a positive judgment is made at SA9, or after SA11 has been carried out, the control of the CPU goes to SA12 to implement a common oscillometric-type blood-pressure determining algorithm so as to determine a mean blood pressure $BP_{MEAN}$ and a diastolic blood pressure $BP_{DIA}$. More specifically described, first, the CPU reads in respective one-heartbeat lengths of the first cuff-pressure signal SC1 and the second pulse-wave signal SM2, like at SA7 and SA8, subsequently determines an amplitude A of a heartbeat-synchronous pulse of the second cuff pulse wave represented by the second pulse-wave signal SM2, and determines the mean blood pressure $BP_{MEAN}$ and the diastolic blood pressure $BP_{DIA}$ based on the change of the amplitudes A.

Then, at SA13, the CPU judges whether the determination of the blood pressure values BP has ended. If a negative judgment is made at SA13, the control goes back to SA12. On the other hand, if a positive judgment is made at SA13, the control goes to SA14 to place the solenoid valve 42 in its opening position and place the switch valve 26 in its quick-deflation position, so as to release the first cuff pressure PC1 and the second cuff pressure PC2 each down to an atmospheric pressure.

Subsequently, at SA15, the CPU operates the display device 68 to display the systolic, mean, and diastolic blood pressure values $BP_{SYS}$, $BP_{MAN}$, and $BP_{DIA}$ determined at SA11 and S12. Thus, the present control routine is finished.

In the above-described embodiment, if the solenoid valve 42 is placed in the opening or connecting position, the pressurized air supplied from the air pump 34 can be supplied to the second rubber bag 14 and, subsequently, if the solenoid valve 42 is placed in the closing or disconnecting position, the pulsation transmitted from the artery 20 of the region where the cuff 12 is worn, to the first rubber bag 16 cannot be transmitted from the first piping 24 via the second piping 36 to the second rubber bag 14. Therefore, a clear change of the respective amplitudes A of the successive heartbeat-synchronous pulses of the second cuff pulse wave that are successively detected by the second rubber bag 14, can be obtained. Thus, the accuracy of measurement of systolic blood pressure $BP_{SYS}$ is improved.

Next, there will be described another embodiment of the present invention. In the following description, the same reference numerals as used in the preceding embodiment are used to designate the corresponding elements of the present embodiment, and the explanation thereof is omitted.

Figure 4:
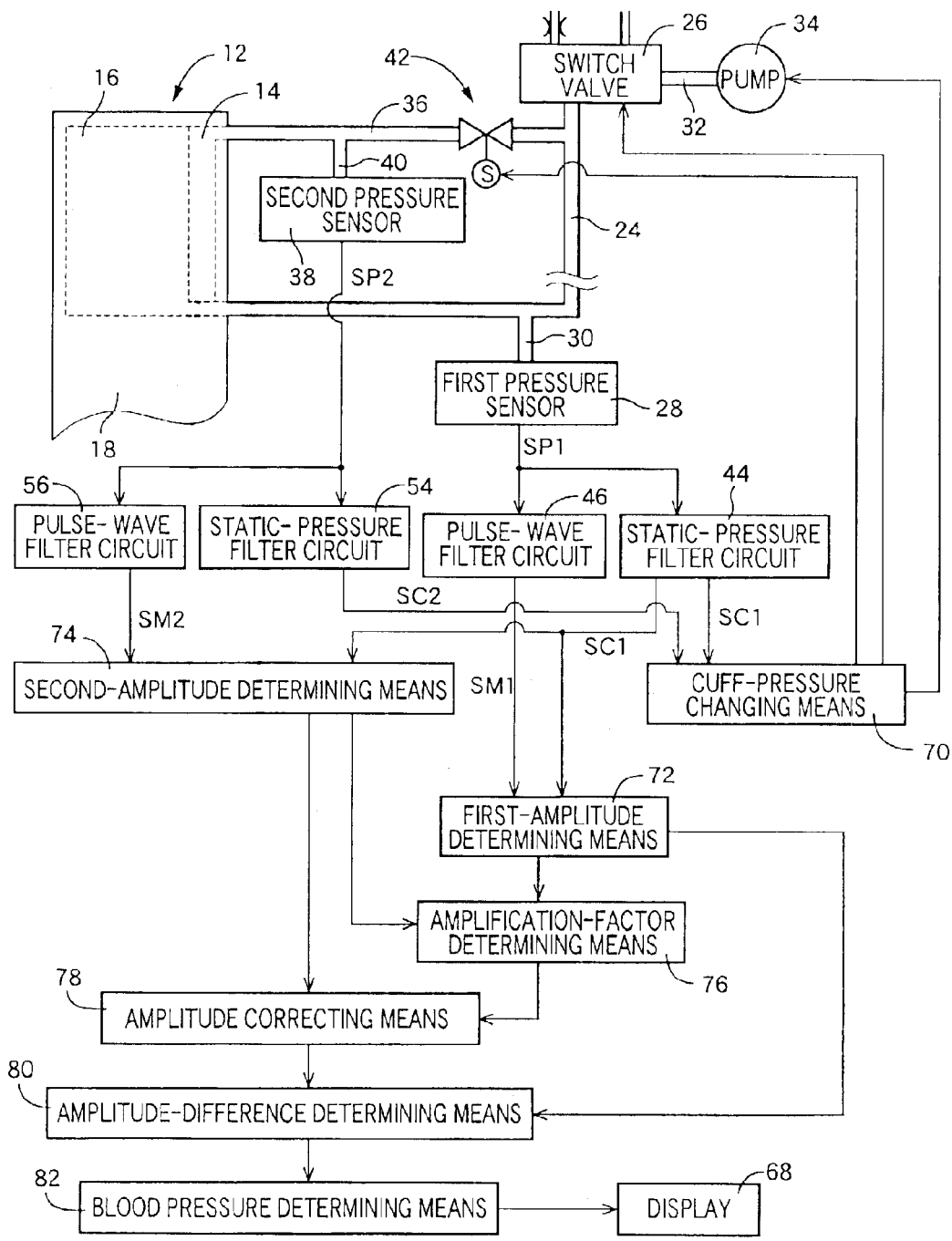
FIG. 4 is a diagrammatic view for explaining essential control functions of a CPU of a different blood pressure measuring apparatus than the blood pressure measuring apparatus of FIG. 1.

FIG. 4 is a diagrammatic view for explaining essential control functions of a CPU 62 of another blood pressure measuring apparatus different than the above-described blood pressure measuring apparatus.

A cuff-pressure changing device or means 70 operates an air pump 34 and switches a switch valve 26 to its pressure-supply position, and additionally places a solenoid valve 42 in its opening position, so as to start quick increasing of a first cuff pressure PC1 and a second cuff pressure PC2. When the second cuff pressure PC2 represented by the second cuff pressure signal SC2 continuously supplied from a static-pressure filter circuit 54 has reached a prescribed first target pressure PCM1, the cuff-pressure changing means 70 places the solenoid valve 42 in its closing position, so that the second cuff pressure PC2 is maintained at the first target pressure PCM1 and the quick increasing of the first cuff pressure PC1 is further continued. Meanwhile, when the first cuff pressure PC1 represented by the first cuff pressure signal SC1 continuously supplied from a static-pressure filter circuit 44 has reached a prescribed second target pressure PCM2, the cuff-pressure changing means 70 stops the operation of the air pump 34 and switches the switch valve 26 to its slow-deflation position, so that the first cuff pressure PC1 is decreased slowly at a prescribed rate of about 3 mmHg/sec, down to a prescribed measurement-end pressure $PC_E$ that would be sufficiently lower than a diastolic blood pressure $BP_{DIA}$ of the subject. When the first cuff pressure PC1 becomes equal to the measurement-end pressure $PC_E$, the cuff-pressure changing means 70 places the solenoid valve 42 in its opening position and switches the switch valve 26 to its quick-deflation position, so that the first and second cuff pressures PC1, PC2 are quickly decreased down to an atmospheric pressure.

A first amplitude determining device or means 72 determines, as a first amplitude A1, an amplitude of each of successive heartbeat-synchronous pulses of a first cuff pulse wave represented by a first pulse wave signal SM1 continuously supplied from a pulse-wave filter circuit 46 while the first cuff pressure PC1 is slowly decreased by the cuff-pressure changing means 70. The first amplitude determining means 72 stores, in a prescribed memory area of the RAM 66, the thus determined first amplitude A1 of each heartbeat-synchronous pulse, together with a value of the first cuff pressure PC1 at the time when the each heartbeat-synchronous pulse is detected by the static-pressure filter circuit 44.

When the first cuff pressure PC1 is slowly decreased in a pressure range higher than a systolic blood pressure $BP_{SYS}$ of the subject that will be determined by a blood pressure determining means 82, described later, the pressing pressure of the cuff 12 stops the flow of blood in an artery 20 under the cuff 12. More specifically described, no pulsation occurs to a distal-side or downstream-side portion of an underlying portion of the artery 20 that underlies the cuff 12 being wound around the ankle. However, even if the first cuff pressure PC1 may be decreased in the pressure range higher than the systolic blood pressure $BP_{SYS}$ of the subject, some pulsation occurs to an upstream-side portion of the underlying portion of the artery 20. This pulsation becomes bigger as the pressing pressure of the cuff 12 is lowered. Since this pulsation is transmitted to the first rubber bag 16, the first amplitudes A1 show a considerably great magnitude even at the commencement of the slow decreasing of the first cuff pressure PC1, and accordingly do not show a clear rising point (i.e., increasing point).

A second amplitude determining device or means 74 determines, as a second amplitude A2, an amplitude of each of successive heartbeat-synchronous pulses of a second cuff pulse wave represented by a second pulse wave signal SM2 continuously supplied from a second pulse wave filter circuit 56 while the first cuff pressure PC1 is slowly decreased by the cuff-pressure changing means 70. The second amplitude determining means 74 stores, in another prescribed memory area of the RAM 66, the thus determined second amplitude A2 of each heartbeat-synchronous pulse, together with a value of the first cuff pressure value PC1 at the time when the each heartbeat-synchronous pulse is detected.

An amplification-factor determining device or means 76 determines an amplification factor N (N is not smaller than 1) that amplifies the second pressure P2 detected by the second pressure sensor 38, so that each of the second amplitudes A2 determined by the second amplitude determining means 74 based on the second cuff pulse wave detected in a blood-flow stopping pressure range in which the flow of blood in the artery 20 is stopped by being pressed by the cuff 12, is substantially equal to a corresponding one of the first amplitudes A1 determined by the first amplitude determining means 72 based on the first cuff pulse wave detected in the blood-flow stopping pressure range. The blood-flow stopping pressure range is a pressure range in which the pressing pressure of the cuff 12, i.e., the first cuff pressure PC1 is decreased from the second target pressure PCM2 to a reference pressure $P_B$ that is not lower than a systolic blood pressure $BP_{SYS}$ of the subject. The reference pressure $P_B$ may be a widely applicable value that is pre-determined based on respective systolic blood pressure values of a number of patients; a value that is predetermined based on an age, etc. of the subject; a value that is inputted in advance through an input device; or a value that is determined based on a fact that a rate of change of each of the second amplitudes A2 determined by the second amplitude determining means 74 exceeds a prescribed value.

An amplitude correcting device or means 78 corrects each of the second amplitudes A2 determined by the second amplitude determining means 74, by multiplying the each second amplitude A2 by the amplification factor N determined by the amplification-factor determining means 76 (hereinafter, the thus corrected second amplitude will be referred to as the "corrected second amplitude A2-1").

An amplitude-difference determining device or means 80 determines an amplitude difference ΔA by subtracting each of the first amplitudes A1 determined by the first-amplitude determining means 72, from a corresponding one of the corrected second amplitudes A2-1 determined by the amplitude correcting means 78 based on the second amplitudes A2. More specifically described, since the second rubber bag 14 receives, via the shield plate 22, the pressure oscillation occurring to the first rubber bag 16, each second amplitude A2 contains a component corresponding to the pressure oscillation of the first rubber bag 16. However, each amplitude difference ΔA is obtained by removing, from each second amplitude A2 (i.e., the amplitude of each heartbeat-synchronous pulse of the second cuff pulse wave as the pressure oscillation transmitted to the second rubber bag 14), the influences of the corresponding first amplitude A1 (i.e., the amplitude of each heartbeat-synchronous pulse of the first cuff pulse wave as the pressure oscillation transmitted to the first rubber bag 16). Therefore, the amplitude difference values ΔA obtained in a range in which the first cuff pressure PC1 is higher than the systolic blood pressure $BP_{SYS}$ are substantially equal to zero, and accordingly show a clear rising point corresponding to the systolic blood pressure $BP_{SYS}$.

A blood pressure determining device or means 82 determines blood pressure values BP of a living subject based on the change of amplitude difference values ΔA determined by the amplitude-difference determining means 80. More specifically described, the blood pressure determining means 82 identifies a rising point of a curve representing the change of amplitude difference values ΔA with respect to the first cuff pressure PC1, and determines, as a systolic blood pressure $BP_{SYS}$ of the subject, a value of the first cuff pressure PC1 at the time of detection of the rising point. The rising point of the curve can be identified in such a manner that a regression line is determined based on a prescribed number of amplitude difference values ΔA and a rate of change of the slope of the regression line exceeds a prescribed value, or in such a manner that one of the amplitude difference values ΔA exceeds a prescribed reference value that is equal to about 10% of the greatest value of the amplitude difference values ΔA. In addition, the blood pressure determining means 82 determines, as a mean blood pressure $BP_{MEAN}$ of the subject, a value of the first cuff pressure PC1 at the time of detection of the greatest one of the first amplitudes A1 or the second amplitudes A2; and determines a diastolic blood pressure $BP_{DIA}$ of the subject according to a common oscillometric method, i.e., based on the change of the amplitude difference values ΔA, the first amplitudes A1, or the second amplitudes A2. The thus determined systolic, mean, and diastolic blood pressure values $BP_{SYS}$, $BP_{MEAN}$, $BP_{DIA}$ are displayed on the display device 68.

Figure 5:
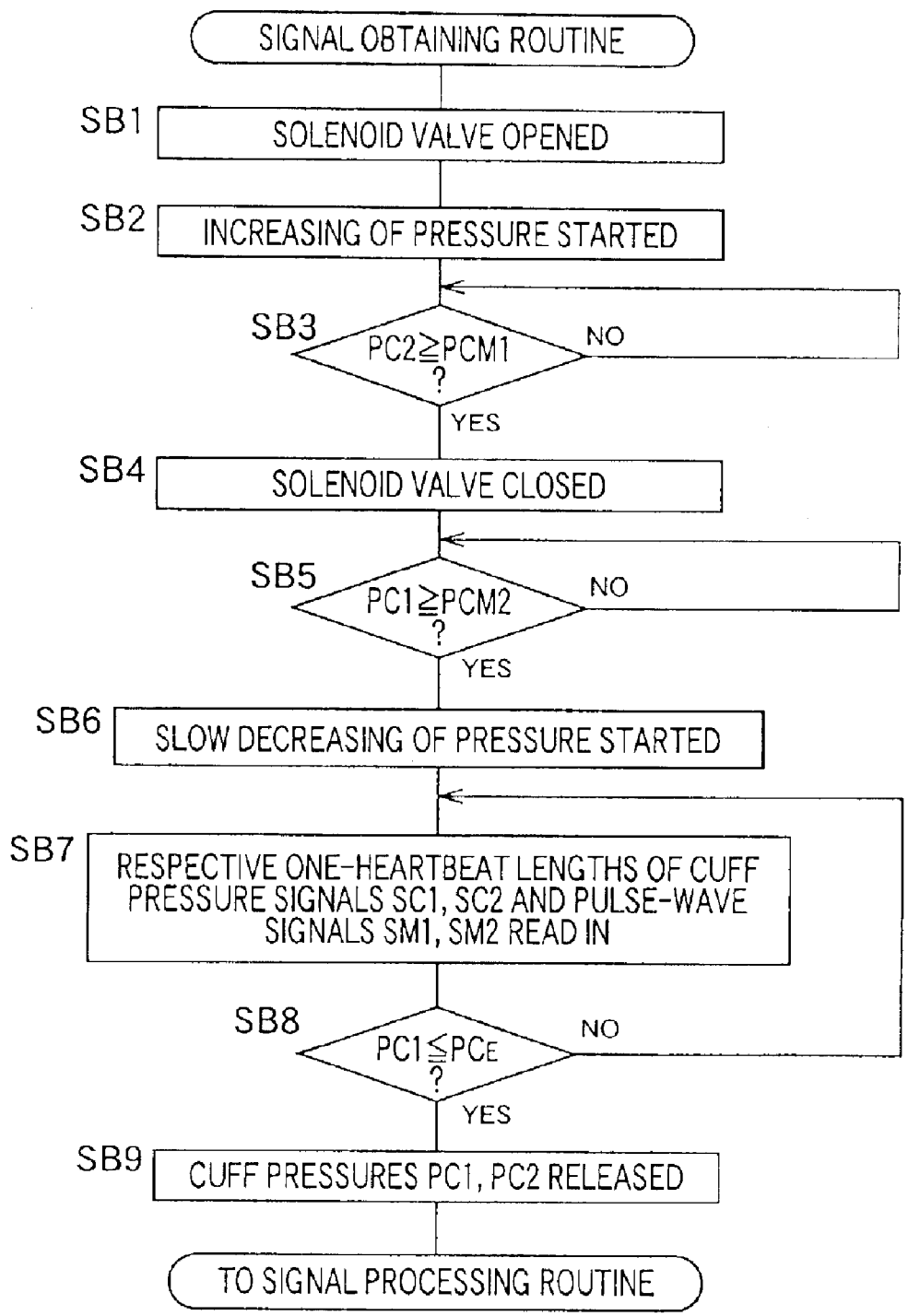
FIG. 5 is a flow chart representing a portion of the essential control functions of the CPU, shown in FIG. 4, that is, a signal obtaining routine.
Figure 6:
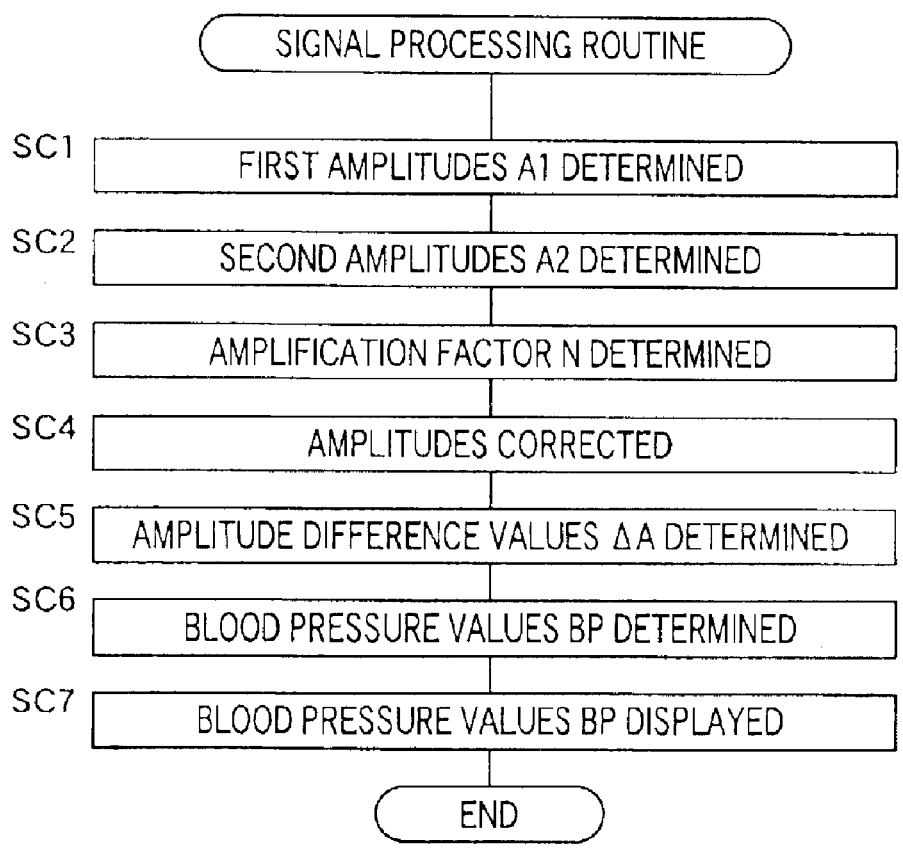
FIG. 6 is a flow chart representing another portion of the essential control functions of the CPU, shown in FIG. 4, that is, a signal processing routine.

FIGS. 5 and 6 are flow charts representing the essential control functions of the CPU 62, shown in FIG. 4; FIG. 5 shows a signal obtaining routine, and FIG. 6 shows a signal processing routine.

First, the CPU implements the signal obtaining routine of FIG. 5. In FIG. 5, SB1 through SB6 are identical with SA1 through SA6 of FIG. 3. Therefore, as a result of implementation of SB1 through SB6, the second cuff pressure PC2 is changed to, and maintained at, a pressure that would be somewhat lower than a diastolic blood pressure $BP_{DIA}$ of the subject, and the first cuff pressure PC1 is first quickly increased up to a second target pressure PCM2 that would be able to stop the flow of blood in the artery 20 and subsequently is slowly decreased at a rate of about 3 mmHg/sec.

At SB7, the CPU reads in respective one-heartbeat lengths of the first cuff-pressure signal SC1 continuously supplied from the static-pressure filter circuit 44, the first pulse-wave signal SM1 continuously supplied from the pulse-wave filter circuit 46, the second cuff-pressure signal SC2 continuously supplied from the static-pressure filter circuit 54, and the second pulse-wave signal SM2 supplied from the pulse-wave filter circuit 56.

Subsequently, at SB8, the CPU judges whether the first cuff pressure PC1 has reached a prescribed measurement-end pressure $P_{CE}$ that would be sufficiently lower than a diastolic blood pressure $B_{PDIA}$ of the subject. If a negative judgment is made at SB8, SB7 and SB8 are repeated, while the CPU continues reading in the first and second cuff-pressure signals SC1, SC2 and the first and second pulse-wave signals SM1, SM2. On the other hand, if a positive judgment is made at SB8, the control goes to SB9 to switch the switch valve 26 to its quick-deflation position and place the solenoid valve 42 in the opening position and thereby release the first and second cuff pressures down to an atmospheric pressure. In FIG. 5, SB1 through SB6, SB8, and SB9 correspond to the cuff-pressure changing means 70.

Then, the CPU implements the signal processing routine of FIG. 6. In FIG. 6, first, the CPU carries out SC1 corresponding to the first amplitude determining means 72. At SC1, the CPU determines a first amplitude A1 of each of the successive heartbeat-synchronous pulses of the first cuff pulse wave represented by the first pulse-wave signal SM1 read in at SB7 of FIG. 5, and stores, in a prescribed memory area of the RAM 66, the thus determined first amplitude $A_1$ of the each heartbeat-synchronous pulse, with a value of the first cuff pressure PC1 at the time of occurrence of the each heartbeat-synchronous pulse having the determined first amplitude A1.

Subsequently, at SC2 corresponding to the second amplitude determining means 74, the CPU determines a second amplitude A2 of each of the successive heartbeat-synchronous pulses of the second pulse wave represented by the second pulse-wave signal SM2 read in at SB7 of FIG. 5, and stores, in another prescribed memory area of the RAM 66, the thus determined second amplitude A2 of the each heartbeat-synchronous pulse, with a value of the first cuff pressure PC1 at the time of occurrence of the each heartbeat-synchronous pulse having the determined second amplitude A2.

Subsequently, at SC3 corresponding to the amplification-factor determining means 76, the CPU determines an amplification factor N that assures that each of the second amplitudes A2 determined at SC2 based on the second cuff pulse wave detected in a pressure range in which the first cuff pressure PC1 is slowly decreased from the second target pressure PCM2 to a reference pressure $P_B$ that is prescribed at, e.g., 210 mmHg, is substantially equal to a corresponding one of the first amplitudes A1 determined at SC1 based on the first cuff pulse wave detected in the same pressure range. For example, the CPU determines, as the amplification factor N, a value obtained by dividing an average of the first amplitudes A1 obtained based on the first cuff pulse wave detected in the above-indicated pressure range, by an average of the second amplitudes A2 obtained based on the second cuff pulse wave detected in the same pressure range.

Subsequently, at SC4 corresponding to the amplitude correcting means 78, the CPU multiplies each of the second amplitudes A2 successively determined at SC2, by the amplification factor N determined at SC3, thereby obtaining respective corrected second amplitudes A2-1 for the successive heartbeat-synchronous pulses of the second cuff pulse wave. The thus obtained corrected second amplitudes A2-1 are substantially equal to the corresponding first amplitudes A1 determined at SC1 for the successive heartbeat-synchronous pulses of the first cuff pulse wave.

Then, at SC5 corresponding to the amplitude-difference determining means 80, the CPU subtracts, from each of the corrected second amplitudes A2-1 determined at SC4, a corresponding one of the first amplitudes A1 determined at SC1, thereby determining an amplitude difference ΔA for each of the successive heartbeat-synchronous pulses of the first or second cuff pulse waves.

Subsequently, the control of the CPU goes to SC6 and SC7 corresponding to the blood pressure determining means 82. First, at SC6, the CPU determines blood pressure values BP (i.e., systolic, mean, and diastolic blood pressure values $BP_{SYS}$, $BP_{MEAN}$, $BP_{DIA}$) of the subject based on the change of the amplitude differences ΔA determined at SC5, the change of the first amplitudes A1, or the change of the second amplitudes A2. For example, the CPU identifies one of the amplitude difference values ΔA, successively obtained during the decreasing of the pressing pressure, that first exceeds a reference value equal to 10% of the greatest one of the amplitude differences ΔA, and determines, as a systolic blood pressure $BP_{SYS}$ of the subject, a value of the first cuff pressure PC1 at the time of detection of the heartbeat-synchronous pulse corresponding to the identified amplitude difference value ΔA. In addition, the CPU determines, as a mean blood pressure $BP_{MEAN}$ of the subject, a value of the first cuff pressure PC1 at the time of detection of the greatest one of the amplitude differences ΔA or the first amplitudes A1; and determines a diastolic blood pressure $BP_{DIA}$ of the subject according to a common oscillometric method, i.e., based on the change of the amplitude differences ΔA or the first amplitudes A1.

Subsequently, at SC7, the CPU operates the display device 68 to display the systolic, mean, and diastolic blood pressure values $BP_{SYS}$, $BP_{MEAN}$, $BP_{DIA}$ determined at SC6. Thus, the present routine is finished.

In the above-described embodiment, the amplitude correcting means 78 (SC4) corrects the second amplitudes A2 obtained from the second rubber bag 14 in the pressure range in which the flow of blood in the artery 20 of the region where the cuff 12 is worn is stopped, so that each of the corrected second amplitudes A2-1 is substantially equal to a corresponding one of the first amplitudes A1 obtained from the first rubber bag 16. The amplitude-difference determining means 80 (SC5) determines the amplitude difference values ΔA between the corrected second amplitudes A2-1 determined by the amplitude correcting means 78 (SC4) and the first amplitudes A1 obtained from the first rubber bag 16. Thus, the amplitude difference values ΔA show a clear rising point. Then, the blood pressure determining means 82 (SC6 and SC7) determines the systolic blood pressure $BP_{SYS}$ based on the change of the amplitude difference values ΔA determined by the amplitude-difference determining means 80 (SC5). Therefore, the systolic blood pressure $BP_{SYS}$ enjoys a high accuracy.

Figure 7:
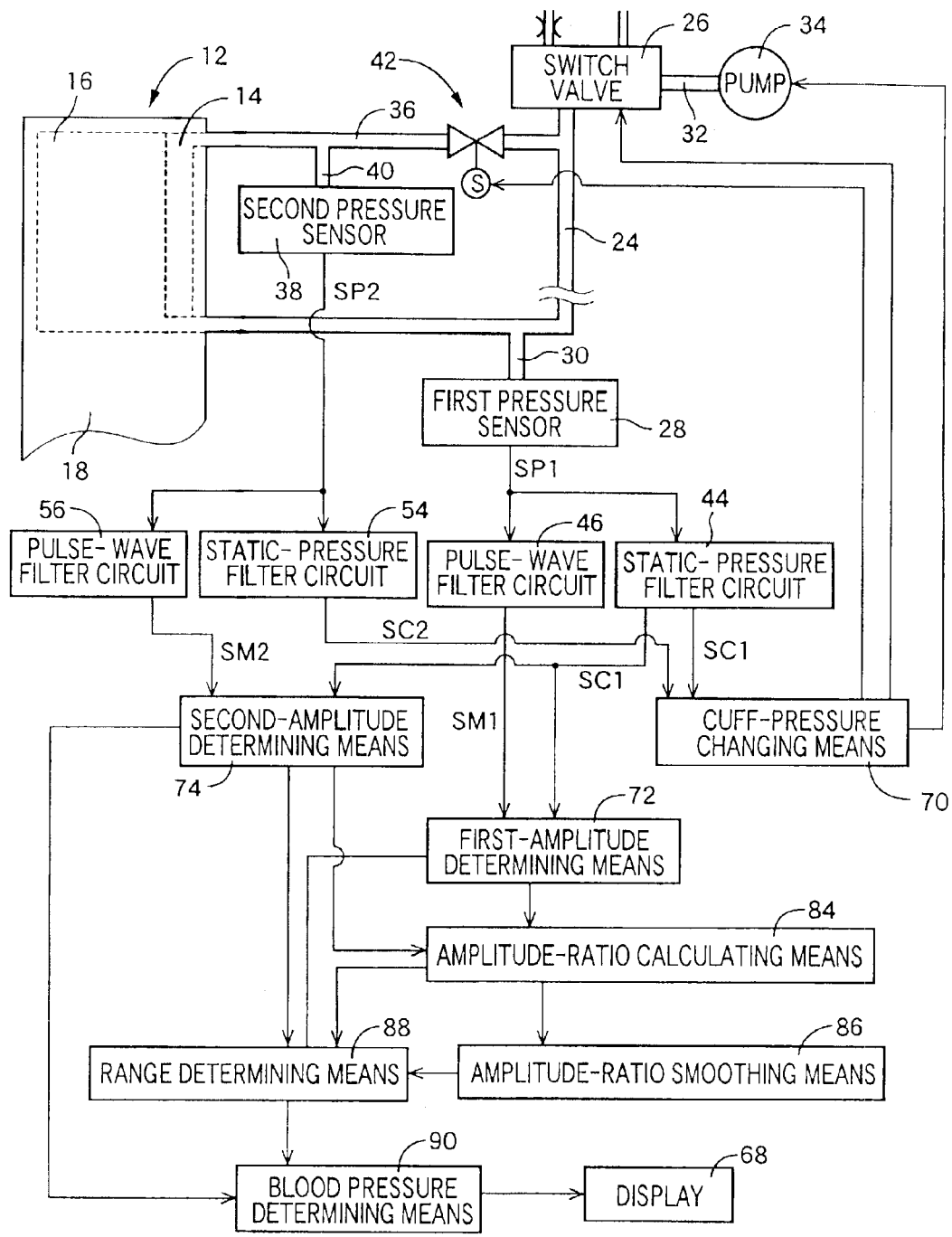
FIG. 7 is a diagrammatic view for explaining essential control functions of a CPU of a different blood pressure measuring apparatus than the above-indicated two blood pressure measuring apparatuses.

Next, there will be described yet another embodiment of the present invention. FIG. 7 is a diagrammatic view for explaining essential control functions of a CPU 62 of yet another blood pressure measuring apparatus different than the above-described two blood pressure measuring apparatuses. In FIG. 7, a cuff-pressure changing device or means 70, a first amplitude determining device or means 72, and a second amplitude determining device or means 74 have the same functions as those of the counter parts 70, 72, 74 shown in FIG. 4, respectively.

An amplitude-ratio calculating device or means 84 calculates a ratio, r, of one of each first amplitude A1 determined by the first amplitude determining means 72 and a corresponding second amplitude A1 determined by the second amplitude determining means 74 to the other of the each first amplitude $A_1$ and the corresponding second amplitude A2 (i.e., r=A1/A2 or A2/A1). Here, it is noted that each first amplitude $A_1$ and a corresponding second amplitude $A_2$ from which a ratio r is calculated are obtained from respective heartbeat-synchronous pulses of the first and second cuff pulse waves that are produced by a same pulsation of the artery 20. That is, each second amplitude $A_2$ used to calculate a ratio r is obtained from a heartbeat-synchronous pulse of the second cuff pulse wave that is detected at substantially the same time as the time of detection of a heartbeat-synchronous pulse of the first cuff pulse wave from which a first amplitude $A_1$, used to calculate the ratio r, is obtained. Though amplitude ratios r may be determined for all the first amplitudes $A_1$ determined by the first amplitude determining means 72 and all the corresponding second amplitudes $A_2$ determined by the second amplitude determining means 74, amplitude ratios r, or smoothed amplitude ratios r', described below, may be determined for only a portion of a pre-selected ones of (a) the first amplitudes A1 or (b) the second amplitudes A2 which portion falls within a range which is determined in advance by a range determining means 88, described later.

As explained previously, even in the state in which the first cuff pressure PC1 is higher than a systolic blood pressure $BP_{SYS}$ of the subject, the pressure oscillation caused by the arterial pulsation is transmitted to the proximal end of the first rubber bag 16, and accordingly the curve representing the change of first amplitude values A1 does not show a clear rising point at the systolic blood pressure $BP_{SYS}$. Meanwhile, in the same state as indicated above, the second rubber bag 14 only receives the pressure oscillation transmitted from the first rubber bag 16 in an indirect or weakened way. On the other hand, in the state in which the first cuff pressure PC1 is lower than the systolic blood pressure $BP_{SYS}$, the second rubber bag 14 directly receives the pulsation of the artery 20 located under the cuff 12, and accordingly the curve representing the change of second amplitude values A2 shows a clearer rising point at the systolic blood pressure $BP_{SYS}$ than the curve representing the change of first amplitude values A1. Since, however, the second rubber bag 14 receives the pressure oscillation caused in the first rubber bag 16, the second amplitude values A2 each contain a component representing the pressure oscillation caused in the first rubber bag 16 and, because of this component, the rising point on the curve representing the change of second amplitude values A2 is more or less unclear. In contrast thereto, since the amplitude ratios r are obtained from the first amplitudes A1 and the second amplitudes A2, the above-indicated component is offset and accordingly the curve representing the change of amplitude ratios r shows a clear rising point.

An amplitude-ratio smoothing device or means 86 smoothes the amplitude ratios r calculated by the amplitude-ratio calculating means 84, according to a well-known mathematical method, such as median-filter method, moving-average method, or smoothing-differentiation method, and thus provides the smoothed amplitude ratios r'. In the median-filter method, each of the amplitude ratios r which are sequentially calculated is replaced with a median of a predetermined number (e.g., 3 or 5) of amplitude ratios r consisting of the each ratio r and respective same numbers (e.g., 1 or 2) of ratio or ratios r preceding and following the each ratio r. In the smoothing-differentiation method, each of the amplitude ratios r which are sequentially calculated is differentiated by obtaining a linear sum of central differences, according to the following Expression 1:

$$y_{(k)} = d/2 \cdot \sum_{n=1}^{N} C_n \{x_{(k+n)} - x_{(k-n)}\} \quad \text{(Expression 1)}$$

where d is a value determined based on a sampling period T; N is a degree; and $C_n$ is a coefficient.

For example, d=1/T, N=1, and $C_1$=1. Expression 1 indicates that the smoothing-differentiation method consists of only calculations of low-degree addition and subtraction. Since this method shows good results, it is known as a useful method for processing a signal obtained from a living being.

The curve representing the change of amplitude ratios r may temporarily (or shortly) change greatly at a point different from a point at a systolic blood pressure $BP_{SYS}$ of the subject. In the case where the systolic blood pressure $BP_{SYS}$ is determined based on the curve representing the change of amplitude ratios r, the systolic blood pressure $BP_{SYS}$ may be erroneously determined based on the above-indicated temporary great change. To solve this problem, the amplitude-ratio smoothing means 86 smoothes the temporary great change that may occur to the curve representing the amplitude ratios.

The range determining means 88 determines a rising range for a pre-selected ones of (a) the first amplitudes A1 or (b) the second amplitudes A2, so that a blood pressure determining means 90, described below, determines a systolic blood pressure $BP_{SYS}$ of the subject based on a portion of the amplitude ratios r or the smoothed amplitude ratios r' that is calculated from a portion of the pre-selected first or second amplitudes A1 or A2 that falls in the thus determined rising range. The rising range may be defined as a high-pressure range of the first cuff pressure PC1 that is higher than a pressure corresponding to the peak (i.e., the greatest value) of the pre-selected first or second amplitudes A1 or A2. Thus, even if the curve representing the amplitude ratios r or the smoothed amplitude ratios r' may largely change in a low-pressure range where the slow decreasing of the first cuff pressure PC1 ends, a low-pressure range of the first cuff pressure PC1 that is lower than the pressure corresponding to the peak of the pre-selected first or second amplitudes A1 or A2, is excluded from the rising range, and accordingly the determination of an erroneous systolic blood pressure $BP_{SYS}$ can be prevented. That is, the blood pressure determining means 90 can determine a systolic blood pressure $BP_{SYS}$ of the subject based on the amplitude ratios r or the smoothed amplitude ratios r' that are calculated from a portion of the pre-selected first or second amplitudes A1 or A2 that falls within the thus determined rising range.

The blood pressure determining means 90 determines a systolic blood pressure $BP_{SYS}$ of the ankle 19 of the subject, based on the amplitude ratios r that are calculated by the amplitude-ratio calculating means 84 from a portion of the pre-selected first or second amplitudes A1 or A2 that falls within the rising range determined by the range determining means 88, or based on the smoothed amplitude ratios r' that are calculated by the amplitude-ratio smoothing means 86 from a portion of the pre-selected first or second amplitudes A1 or A2 that falls within the rising range determined by the range determining means 88. As explained previously, the curve representing the amplitude ratios r or the smoothed amplitude ratios r' largely changes at a systolic blood pressure $BP_{SYS}$ of the subject. Therefore, the blood pressure determining means 90 determines a systolic blood pressure $BP_{SYS}$ of the ankle 19 based on a fact that the change of each of the amplitude ratios r or the smoothed amplitude ratios r', obtained from the above-indicated rising range, exceeds a reference value. For example, the blood pressure determining means 90 calculates a change ratio, d, for each of the above-indicated portion of the smoothed amplitude ratios r' (or of the amplitude ratios r), selects all the change ratios d that are greater than a reference change ratio, $d_{ST}$, determines one of the thus selected great change ratios d such that the thus determined one great change ratio d corresponds to the highest one of the first cuff pressure values PC1 respectively corresponding the selected great change ratios d, and finally determines, as a systolic blood pressure $BP_{SYS}$ of the subject, the highest first cuff pressure value PC1 corresponding to the thus selected one change ratio d. In addition, the blood pressure determining means 90 determines, according to the common oscillometric method, a mean blood pressure $BP_{MEAN}$ and a diastolic blood pressure $BP_{DIA}$, based on the first amplitudes A1 determined by the first amplitude determining means 72 or the second amplitudes A2 determined by the second amplitude determining means 74. The determining means 90 operates the display device 68 to display the thus determined blood pressure values $BP_{SYS}$, etc.

FIG. 8 is a flow chart representing a portion of the control functions of the CPU 62, shown in FIG. 7, that is, a signal processing routine.

The signal processing routine of FIG. 8 is implemented, in place of the signal processing routine of FIG. 6, after the signal obtaining routine of FIG. 5.

In FIG. 8, first, the CPU carries out SD1 corresponding to the first amplitude determining means 72. At SD1, the CPU determines a first amplitude A1 of each of successive heartbeat-synchronous pulses of the first cuff pulse wave represented by the first pulse-wave signal SM1 successively read in at SB7 of FIG. 5, and stores, in a prescribed memory area of the RAM 66, the thus determined first amplitude A1 of the each heartbeat-synchronous pulse, with a first cuff pressure value PC1 at the time of occurrence of the each heartbeat-synchronous pulse having the determined first amplitude A1.

Subsequently, at SD2 corresponding to the second amplitude determining means 74, the CPU determines a second amplitude A2 of each of successive heartbeat-synchronous pulses of the second cuff pulse wave represented by the second pulse-wave signal SM2 successively read in at SB7 of FIG. 5, and stores, in another prescribed memory area of the RAM 66, the thus determined second amplitude A2 of the each heartbeat-synchronous pulse, with a first cuff pressure value PC1 at the time of occurrence of the each heartbeat-synchronous pulse having the determined second amplitude A2.

Then, at SD3 corresponding to the amplitude-ratio calculating means 84, the CPU calculates a ratio r of the first amplitude A1 of each of the successive pulses of the first cuff pulse wave, determined at SD1, to the second amplitude A2 of a corresponding one of the successive pulses of the second cuff pulse wave, determined at SD2, i.e., r=A1/A2.

Subsequently, at SD4 corresponding to the amplitude-ratio smoothing means 86, the CPU smoothes, according to, e.g., the above-described median-filter method, the amplitude ratios r, calculated at SD3, and provides the smoothed amplitude ratios r' for the respective pulses of the first and second cuff pulse waves.

At SD5 corresponding to the range determining means 88, the CPU determines the greatest one of the first amplitudes A1 determined at SD1, determines a rising range which is higher than a cuff pressure PC1 at the time of occurrence of the greatest first amplitude A1, and selects, from the smoothed amplitude ratios r' calculated at SD4 for the respective pulses of the first and second cuff pulse waves, the smoothed amplitude ratios r' obtained from a portion of the pulses of the first and second cuff pulse waves that occurred while the cuff pressure PC1 changed in the rising range.

Then, the control goes to SD6 and SD7 corresponding to the blood pressure determining means 90. First, at SD6, the CPU determines a systolic blood pressure $BP_{SYS}$ of the subject based on the smoothed amplitude ratios r' selected at SD5. For example, the control device 40 calculates a change ratio, d $(=r_1'/r_2')$, of each $(r_1')$ of the selected smoothed amplitude ratio r', to the following selected smoothed amplitude ratio r' $(r_2')$, selects one or more change ratios d greater than a reference change ratio, $d_{ST}$, determines one of the thus selected great change ratios d such that the thus determined one great change ratio d corresponds to the highest one of the cuff pressure values PC1 respectively corresponding to the selected great change ratios d, and finally determines, as a systolic blood pressure $BP_{SYS}$ of the subject, the highest cuff pressure PC1 corresponding to the determined one great change ratio d. In addition, the CPU determines, according to the common oscillometric method, a mean blood pressure $BP_{MEAN}$ and a diastolic blood pressure $BP_{DIA}$ of the subject, based on the first amplitudes A1 or the second amplitudes A2.

Subsequently, at SD7, the CPU operates the display device 68 to display the systolic, mean, and diastolic blood pressure values $BP_{SYS}$, $BP_{MEAN}$, and $BP_{DIA}$ determined at SD6. Thus, the present routine is finished.

In the above-described embodiment, the first amplitude determining means 72 (SD1) determines the respective first amplitudes A1 of successive heartbeat-synchronous pulses of the first cuff pulse wave produced in the first rubber bag 16 while the pressure in the first bag 16 is slowly changed; the second amplitude determining means 74 (SD2) determines the respective second amplitudes A2 of successive heartbeat-synchronous pulses of the second cuff pulse wave produced in the second rubber bag 14 while the pressure of the first rubber bag 16 is slowly changed; the amplitude-ratio calculating means 84 (SD3) calculates the respective ratios r of the first amplitudes A1 to the second amplitudes A2; and the blood pressure determining means 90 (SD6 and SD7) determines the systolic blood pressure $BP_{SYS}$ of the subject based on the amplitude ratios r. Since the amplitude ratios r significantly greatly change at the systolic blood pressure $BP_{SYS}$, the blood pressure determining means 90 (SD6 and SD7) can determine the systolic blood pressure $BP_{SYS}$, based on the amplitude ratios r. Thus, the present apparatus can obtain an accurate systolic blood pressure $BP_{SYS}$ of the subject.

While the present invention has been described in detail in its preferred embodiments, by reference to the drawings, it is to be understood that the present invention may otherwise be embodied.

For example, in each of the illustrated embodiments, the cuff 12 is adapted to be wound around the ankle 19. However, the cuff 12 may be so modified as to be wound around a body portion other than the ankle 19, such as a femoral portion or a brachial portion.

In each of the illustrated embodiments, the inflating fluid that inflates the first and second rubber bags 16, 14 is air. However, other sorts of gas, or various sorts of a liquid may be used as the inflating fluid that inflates the first and second rubber bags 16, 14.

In each of the illustrated embodiments, the lengthwise dimension of the second rubber bag 14 is substantially the same as that of the first rubber bag 16. However, since the second bag 14 is for detecting the pulse wave produced from the artery 20 of the body portion around which the cuff 12 is wound, the second bag 14 is just required to be located right above the artery 20. Accordingly, the lengthwise dimension of the second bag 14 may be shorter than that of the first bag 16.

In each of the illustrated embodiments, the second rubber bag 14 is located at the most distal or downstream position of the cuff 12. However, the second bag 14 may be located at a position upstream of the most downstream position, within a downstream-side half portion of the first rubber bag 16. In addition, the second rubber bag 14 may be located at a position downstream of the most downstream position. For example, the second bag 14 may be provided such that the upstream end of the second bag 14 is in contact with the downstream end of the first bag 16. That is, the second bag 14 may be provided such that the second bag 14 does not overlap the first bag 16. In the last case, the shield plate 22 is omitted.

In the first embodiment shown in FIGS. 1 through 3, if the CPU judges at SA10 of FIG. 3 that the rising point of the amplitudes A has occurred, then the CPU determines, at SA11, the current value of the first cuff pressure PC1 as the pressing pressure of the first rubber bag 16, as the systolic blood pressure $BP_{SYS}$ of the subject. However, at that point of time, the second rubber bag 14 is pressed by the first rubber bag 16. Therefore, the static pressure of the second bag 14 is equal to that of the first bag 16. Thus, it is possible to determine the systolic blood pressure $BP_{SYS}$ of the subject based on the static pressure of the second bag 14.

In the second embodiment shown in FIGS. 4 through 6, the amplitude correcting means 78 corrects the second amplitudes A2 determined by the second-amplitude determining means 74, so that the first amplitudes A1 determined by the first-amplitude determining means 72 are substantially equal to the corresponding, corrected second amplitudes A2', respectively. However, it is possible to correct the first amplitudes A1, so that the corrected first amplitudes A1 are substantially equal to the corresponding second amplitudes A2, respectively.

In each of the second and third embodiments, the blood pressure determining means 82, 90 determines the blood pressure values BP by processing the signals after the slow deflation of the cuff 12 has been finished. However, the blood pressure determining means may be so modified as to determine blood pressure values BP by processing the signals while the pressure of the cuff 12 is slowly decreased.

In the third embodiment shown in FIGS. 7 and 8, the range determining means 88 (SD5) determines the rising range, so that the smoothed amplitude ratios r' obtained based on a portion of the first or second amplitudes A1 or A2 that falls within the thus determined rising range is used by the blood pressure determining means 90 (SD6 and SD7) to determine the systolic blood pressure $BP_{SYS}$. However, the range determining means 88 may be omitted, and the systolic blood pressure $BP_{SYS}$ may be determined as follows: The blood pressure determining means 90 determines a change ratio d for each of the smoothed amplitude ratios r' (or each of the amplitude ratios r) in an order starting with the highest one of the cuff pressure values PC1 respectively corresponding to the ratios r' (or the ratios r). In this case, the cuff pressure value PC1 corresponding to the smoothed amplitude ratio r' (or the amplitude ratio r) that first exceeds the reference change ratio $d_{ST}$ may be determined as the systolic blood pressure $BP_{SYS}$. Alternatively, the blood pressure determining means 90 compares each of the smoothed amplitude ratios r' (or each of the amplitude ratios r) with a prescribed threshold value TH in an order starting with the highest one of the cuff pressure values PC1 respectively corresponding to the ratios r' (or the ratios r). In the last case, the cuff pressure value PC1 corresponding to the smoothed amplitude ratio r' (or the amplitude ratio r) that first exceeds the threshold value TH may be determined as the systolic blood pressure $BP_{SYS}$.

It is to be understood that the present invention may be embodied with other changes, improvements and modifications that may occur to a person skilled in the art without departing from the spirit and scope of the invention.

What is claimed is:

1. A blood pressure measuring apparatus, comprising:
   an inflatable cuff including a first inflatable bag adapted to be worn on a body portion of a living subject so as to exclude blood from an artery located in the body portion, and a second inflatable bag adapted to be worn on the body portion, on a distal side of a middle portion of the first inflatable bag, so as to detect a pulse wave produced from the artery;
   a first piping which is connected to the first inflatable bag;
   a second piping which is branched from the first piping and is connected to the second inflatable bag;
   a pump which supplies an inflating fluid to the first and second inflatable bags via the first and second pipings, respectively;
   a blood pressure determining device which determines a blood pressure of the subject based on the pulse wave detected through the second inflatable bag when a pressing pressure of the first inflatable bag is changed; and
   a switching device which is provided in the second piping and which selectively switches the second piping to a connected state in which the second piping is connected to the first piping and to a disconnected state in which the second piping is disconnected from the first piping;
   pressure determining device includes:
   an amplitude correcting means for correcting at least one of (a) respective first amplitudes of respective heartbeat-synchronous pulses of a first pulse wave detected through the first inflatable bag when the pressing pressure of the first inflatable bag is decreased in a blood-flow stopping pressure range in which a flow of blood in the artery is stopped, and (b) respective second amplitudes of respective heartbeat-synchronous pulses of a second pulse wave detected through the second inflatable bag when the pressing pressure of the first inflatable bag is decreased in the blood-flow stopping pressure range, so that each of the corrected amplitudes is substantially equal to a corresponding amplitude of the other of (a) the first amplitudes and (b) the second amplitudes;
   an amplitude-difference determining means for determining an amplitude difference between said each of the corrected amplitudes and said corresponding amplitude of the other of (a) the first amplitudes and (b) the second amplitudes, so that the determined amplitude differences show a rising point; and
   a blood pressure determining means for determining a systolic blood pressure of the subject based on the rising point of the amplitude differences determined by the amplitude-difference determining means.

2. An apparatus according to claim 1, wherein the blood pressure determining means determines, as the systolic blood pressure of the subject, a value of the pressure of the first inflatable bag at a time of detection of the rising point where the amplitude differences determined by the amplitude-difference determining means significantly greatly changes.

3. A blood pressure measuring apparatus comprising:

an inflatable cuff including a first inflatable bag adapted to be worn on a body portion of a living subject so as to exclude blood from an artery located in the body portion, and a second inflatable bag adapted to be worn on the body portion, on a distal side of a middle portion of the first inflatable bag, so as to detect a pulse wave produced from the artery;

a first piping which is connected to the first inflatable bag;

a second Piping which is branched from the first piping and is connected to the second inflatable bag;

a pump which supplies an inflating fluid to the first and second inflatable bags via the first and second pipings, respectively;

a blood pressure determining device which determines a blood pressure of the subject based on the pulse wave detected through the second inflatable bag when a pressing pressure of the first inflatable bag is changed; and a switching device which is provided in the second piping and which selectively switches the second piping to a connected state in which the second piping is connected to the first piping and to a disconnected state in which the second piping is disconnected from the first piping;

wherein the second inflatable bag is provided in a distal-side half portion of the cuff when wound on the body portion of the subject, such that the second inflatable bag is located on a distal side of a first portion of the first inflatable bag and on an inner side of a second portion of the first bag that is located on a distal side of the first potion thereof.

4. A blood pressure measuring apparatus, comprising:

an inflatable cuff including a first inflatable bag adapted to be worn on a body portion of a living subject so as to exclude blood from an artery located in the body portion, and a second inflatable bag adapted to be worn on the body portion, on a distal side of a middle portion of the first inflatable bag, so as to detect a pulse wave produced from the artery;

a first piping which is connected to the first inflatable bag;

a second pining which is branched from the first piping and is connected to the second inflatable bag;

a pump which supplies an inflating fluid to the first and second inflatable bags via the first and second pipings, respectively;

a blood pressure determining device which determines a blood pressure of the subject based on the pulse wave detected through the second inflatable bag when a pressing pressure of the first inflatable bag is changed; and a switching device which is provided in the second piping and which selectively switches the second piping to a connected state in which the second piping is connected to the first piping and to a disconnected state in which the second piping is disconnected from the first piping;

wherein the blood pressure determining device includes:

a first amplitude determining means for determining respective first amplitudes of respective heartbeat-synchronous pulses of a first pulse wave detected through the first inflatable bag when the pressure of the first inflatable bag is changed;

a second amplitude determining means for determining respective second amplitudes of respective heartbeat-synchronous pulses of a second pulse wave detected through the second inflatable bag when the pressure of the first inflatable bag is changed;

an amplitude-ratio determining means for determining an amplitude ratio between each of the first amplitudes determined by the first amplitude determining means and a corresponding one of the second amplitudes determined by the second amplitude determining means; and a blood pressure determining means for determining a systolic blood pressure of the subject based on the amplitude ratios determined by the amplitude-ratio determining means.

5. An apparatus according to claim 4, wherein the blood pressure determining means determines, as the systolic blood pressure of the subject, a value of the pressure of the first inflatable bag at a time when the amplitude ratios determined by the amplitude-ratio determining means significantly greatly changes.

* * * * *